United States Patent [19]

Paquet

[11] 4,126,628

[45] Nov. 21, 1978

[54] ACYLATION OF AMINO ACIDS

[75] Inventor: Alenka M. Paquet, Ottawa, Canada

[73] Assignee: Canadian Patents and Development Limited, Ottawa, Canada

[21] Appl. No.: 781,797

[22] Filed: Mar. 28, 1977

[51] Int. Cl.$^2$ .................... C11C 3/00; C07C 103/52; C07C 101/24; C07C 101/26

[52] U.S. Cl. ...................... 260/404.5; 260/112.5 R; 560/159; 560/169; 562/561

[58] Field of Search .............. 260/404.5 A, 404.5 PA, 260/534 L, 534 R, 534 G, 482 R, 482 C, 112.5 R

[56] References Cited

U.S. PATENT DOCUMENTS

| | | | |
|---|---|---|---|
| 3,317,559 | 5/1967 | Anderson | 260/112.5 R X |
| 3,541,084 | 11/1970 | Hagitani et al. | 260/112.5 R |
| 3,578,641 | 5/1971 | Johnson | 260/112.5 R |
| 3,780,015 | 12/1973 | Hirschmann et al. | 260/112.5 R |
| 3,870,694 | 3/1975 | Fujino et al. | 260/112.5 R |
| 3,880,823 | 4/1975 | Hagitani et al. | 260/112.5 R |
| 4,043,992 | 8/1977 | Fujimoto et al. | 260/112.5 R |

OTHER PUBLICATIONS

Anderson et al., "JACS", vol. 86, pp. 1839–1842 (1964).

*Primary Examiner*—Winston A. Douglas
*Assistant Examiner*—John J. Doll
*Attorney, Agent, or Firm*—Alan A. Thomson

[57] ABSTRACT

N-mono-substituted derivatives of diamino acids are prepared by the reaction of succinimidyl esters of carboxylic acids or substituted carbonic acids with the unprotected diamino acid. The acylation preferentially occurs at the side chain or terminal amino group of the diamino acid. For example, selective acylation of the terminal amino group of lysine occurs without first having protected the 2-amino group. Such acylation has application in the preparation of inter alia $N^6$-palmitoyl-lysine.

12 Claims, No Drawings

ACYLATION OF AMINO ACIDS

FIELD OF THE INVENTION

This invention deals with the acylation of diamino acids to form a peptide linkage between the diamino acid and carboxylic or substituted carbonic acid. The defined acylating agents acylate preferentially, or selectively at high pH, the terminal amino group without the necessity of protecting the less basic or 2-amino group.

DESCRIPTION OF THE PRIOR ART

Several syntheses of fatty N-acylmonoamino acids have been reported using common methods in peptide chemistry such as (a) the chloride method (Bondi, Biochem. J., 17, 53 (1909); Chem. Abstr., 3, 2014V; Ueha et al., Japan Pat. No. 9568, (1956); Chem. Abstr. 52, 14669h (1958); Jungermann et al., J. Am. Chem. Soc. 78, 172 (1956); Takehara et al., J. Am. Chem. Soc. 49, 157 (1972)); (b) the anhydride method (Lorentzen, U.S. Pat. No. 3,074,980 (1963); Chem. Abstr. 59, 4034h, (1963); Heitmann, Europ. J. Biochem., 3, 346, (1968); Fieser et al., J. Am. Chem. Soc. 78, 2825, (1956)); (c) the dicyclohexylcarbodiimide method (Ivaldi et al., Giorn. Biochim. 10, page 549, (1961), Chem. Abstr. Vol. 58, 4643e, (1963)) and (d) the succinimidyl esters method (Lapidot et al., J. Am. Chem. Soc. 86, 1839 (1964)).

Acylation of diamino acids by acyl chlorides or anhydrides gives disubstituted derivatives. (Greenstein and Winitz, in "Chemistry of the Amino Acids", Wiley, N.Y., 1961, Vol. 2, p. 890 and 895. Leclerc and Benoiton, Can. J. Chem. 46, 1047 (1968)). Selective acylation of diamino acids such as lysine can be achieved by the action of an acylating agent upon the copper salt of the amino acid a procedure which is routinely used in order to prevent the acylation of the 2-amino group (Kurz, J. Biol. Chem. 122, 477 (1938)). This route is tedious however.

Japanese workers have recently described two routes claimed to give $N^6$-acyl derivatives of basic amino acids without protecting the alpha-amino group: Ohkawa et al. in Japanese Laid-Open Specification No. 19717/76 claims a process for the manufacture of such compounds using acyl chlorides (such as caproyl, lauroyl, benzoyl) in water or a water-organic solvent mixture employing, e.g., benzene, acetone, methyl ethyl ketone, methanol, or ethanol. Takizawa et al. in U.S. Pat. No. 3,897,466 (1975) obtained $N^6$-acylated lysine derivatives by dehydration of the pertinent salts at high temperatures for the period of 7 hours.

No description of the mechanism is available at present to account for the selectivity claimed by these Japanese workers. In fact, it is impossible to discern a basic distinction between the procedure described by Ohkawa et al. which was claimed to give $N^6$-monosubstituted lysine and that described by Greenstein and Winitz (above) and discussed by Leclerc and Benoiton (Can. J. Chem. 45, 1047 (1968)), which gives a disubstituted product. It would follow from Ohkawa et al. that one mole of acyl chloride reacts with one mole of lysine to form essentially monosubstituted product. However, the applicant has found that upon reacting one mole of lauroyl or caproyl chloride with one mole of lysine, some disubstituted lysine was formed along with monosubstituted lysine, and some lysine was left unreacted. Thus the acyl chloride route is not terminal amino-group specific. Specificity, if present, would have to be an accidental consequence of specific factors or conditions as yet not understood.

Leclerc and Benoiton (above) achieved selective acylation of the side chain amino group of lysine. Only p-nitrophenyl esters of low molecular weight acids used at high pH were found to be selective acylating agents. The mechanism postulated by Leclerc and Benoiton for the discriminatory acylation depends upon the difference in the basicities of the 6- and 2-amino groups of free lysine. Aminolysis of the ester by the more basic 6-amino group is evidently favored at high pH. The only esters used were p-nitrophenyl-acetate, -chloroacetate and -propionate.

Lapidot et al. (Jour. of Lipid Research, Vol. 8, pages 142–145, 1967) found that N-hydroxysuccinimide esters of fatty acids reacted readily with the sodium salt of free monoamino acids in aqueous solution to form the corresponding N-acylamino acids. The only amino acids mentioned were glycine, serine and glutamic acid (monoamino acids).

A procedure which doesn't produce significant amounts of disubstituted product and which, moreover effects substitution only at the terminal amino group of diamino acids is described now as the present invention. Such a method according to this invention is the acylation of free diamino acid by chosen succinimidyl esters at pH over about 10 in an organic or water-organic medium, which is technically simple, allows more ready recovery of the reagents and product, and gives good yields.

SUMMARY OF THE INVENTION

According to this invention, diamino acids are monoacylated with certain esters preferentially at the terminal amino group of the amino acid remote from the carboxyl group by steps comprising (a) preparing the succinimidyl ester of the desired acid, (b) reacting at a pH of at least about 10, said succinimidyl ester with the diamino acid, its ester or oligopeptide thereof to form the amide linkage between the terminal amino group and the acid without significant acylation of the other unprotected amino group, in an inert liquid medium, and (c) recovering the N-acyldiamino acid, ester or oligopeptide thereof as product.

A preferred aspect of the invention is the method wherein (a) the thallium salt of N-hydroxysuccinimide in an inert solvent medium is reacted with acid chloride in approximately equimolar amounts, the acid chloride being selected from fatty acid chlorides and alkylcarbonic acid chlorides, to give the succinimidyl ester, and the thallium chloride precipitate separated, (b) said succinimidyl ester is then reacted in an inert solvent medium with lysine, lysine hydrochloride, or lysine ester, in the presence of alkaline catalyst, to give a pH of about 10–12, the pH subsequently reduced to precipitate reaction product, and (c) N-acyllysine or -lysine ester precipitate recovered, the acylation preferentially occurring on the terminal amino group of lysine.

DETAILED DESCRIPTION

The diamino acids are selected from those having two amino groups separated by at least one methylene group with typical examples being $\alpha,\gamma$-diaminobutyric acid, lysine and ornithine. The examples given below relate to lysine because of its current availability at reasonable cost and balance of properties, but others would be equally operative. Oligopeptides having free amino groups can also be acylated. For example, lysyllysine and alanyllysyllysine can be selectively acylated. The L, D or racemic forms may be used. With the carboxyl unprotected amino acid, an excess of succinimidyl ester can be used, but with the ester form of the amino acid, the relative proportions of reactants should be close to equimolar. The ester form can be for example, methyl, ethyl or succinimidyl.

The carboxylic acid can be any having at least 2 carbon atoms, straight or branched chain, saturated or unsaturated. Suitable fatty acids include hexanoic, octanoic, capric, lauric, myristic, palmitic, palmitoleic, stearic, oleic, ricinoleic, linoleic, arachidic and erucic acid. Fatty acids of 8 to 18 carbon atoms are usually preferred for industrial applications.

Alkyl carbonic acid chlorides such as benzyl chlorocarbonate, t-butyl chlorocarbonate and p-nitrobenzyl chlorocarbonate can also be used to form the succinimidyl ester. These alkyl or aralkyl succinimidyl carbonates react similarly to give, e.g., $N^6$-alkyloxycarbonyllysine derivatives (N-protecting groups in peptide syntheses).

N-hydroxysuccinimde is commercially available and the fatty acid ester thereof can be prepared by reaction with the appropriate fatty acid in the presence of dicyclohexylcarbodiimide. Applicant has found a novel alternative preparative technique necessary in some cases, particularly with acyl chlorides such as alkyl chlorocarbonates, i.e., utilizing the thallium salt of N-hydroxylsuccinimide and reacting this salt with the acyl chloride, the succinimidyl ester then being recovered in excellent yields. Insoluble thallium chloride will form and can be removed, e.g., by filtration. The reaction medium for succinimidyl ester formation can be any suitable solvent such as chloroform, dichloromethane, ether, dimethylformamide etc. The reaction will be complete in about 1 hour at room temperature. The thallium can be recycled.

The succinimidyl ester is then reacted in step (b) with the diamino acid (or salt or ester or oligopeptide thereof) in an inert liquid medium, at a pH of at least about 10 preferably 10–12.5, to form the N-acylamino acid (or ester or oligopeptide). This acylation has been found to occur preferentially at the terminal amino group removed from the carboxyl group. Usually, approximately equimolar amounts of each reactant would be reacted, with a minor excess of the succinimidyl ester giving satisfactory results. The reaction proceeds at room temperature but slightly elevated temperatures, e.g., 25° C. to 50° C. can be used. The reaction is usually complete after about 2 hours at 20° C. at pH over 10.

The reaction medium for acylation may be any inert organic or water-organic solvent such as chloroform, methylene chloride, ethylene dichloride, ethylene glycol, water-acetone, water-alcohol, methylamine, tetrahydrofuran, pyridine, and triethylamine. The same organic solvent as for succinimidyl ester formation can be used but the pH should be raised to at least about 10. The particular solvent medium used is not critical.

A basic catalyst is preferably added in sufficient amounts to achieve the high pH and facilitate the reaction. Amounts of the order of about 2 to 3 equivalents based on the diamino acid are usually used, but these amounts are not critical as long as the required pH is attained. Suitable catalysts include trialkylamines such as trimethyl- and triethylamine, triphenylamine and alkali metal hydroxides or carbonates. The pH of the reaction medium is critical for the selective acylation on the terminal amino group.

When the reaction is substantially complete, the acylated amino acid product can be recovered for example by precipitation by lowering the pH to about 3. This pH change can be accomplished by removal of the basic catalyst (e.g., by evaporating trialkylamine under reduced pressure) and by acidification, e.g., by the addition of mineral acid. The precipitated product is readily removed by filtration or centrifugation, and is usually washed, e.g., with water, and dried. Yields are in the range of about 70 to 95%. Further purification as by crystallization from glacial acetic acid can be carried out if desired.

The reaction medium (mother liquor) will contain regenerated N-hydroxysuccinimide, any residual catalyst and unreacted material and can usually be recycled for further reaction. If desired, the N-hydroxysuccinimide can be recovered and used to prepare succinimidyl ester in step (a), and the solvent medium returned to step (b).

The acylated reaction product will have substantially all of the acylation at the amino group furthest from the carboxylic group, e.g., usually at least 90% at this terminal position. Small amounts of di-acyl derivative may be produced in some cases and for most purposes its presence would be quite acceptable.

The monoacylated reaction product can be combined via the unreacted amino group or via the carboxylic group (free or activated, e.g., as succinimidyl ester) into di- and higher peptides.

These N-acyl amino acid products have utility as surface active agents, or as pharmaceuticals (or intermediates therefor). A few compounds of this type have been used in certain food compositions. Such compounds have also been claimed to have inter alia metabolic stimulating, anti-allergic and wound-healing activity (see U.S. Pat. No. 3,541,135, Nov. 17, 1970, A. Johl et al. and also U.S. Pat. No. 3,551,419, Dec. 29, 1970, Da Re et al.). The $N^6$-alkoxycarbonyl derivatives such as benzyloxycarbonyl would have application in preparing the bronchodilator of U.S. Pat. No. 3,828,018, Dormann.

EXAMPLES AND PREFERRED EMBODIMENTS

The following examples are intended to be illustrative only without limiting the scope of the invention.

EXAMPLE 1

Thallium(I) Salt of N-Hydroxysuccinimide

To a solution of N-hydroxysuccinimide (11.5 g, 0.1 mol, previously dried by evaporation with ethanol and drying under reduced pressure for about 1h) in absolute ethanol (20 ml), thallous ethoxide (24.9 g, 0.1 mol) was added dropwise under vigorous stirring at room temperature. Stirring was continued for 1h and the reaction mixture was allowed to stand at 0° C. overnight. Within this period the yellow precipitate changed to a white semicrystalline mass which was collected by filtration and washed with cold ethanol yielding 31.8 g (quantitative yield) of title compound. A small amount was recrystallized from water-ethanol in order to obtain an analytical sample; mp 208°–210° C. Analysis calcd. for $C_4H_4NO_2Tl$: C 15.08, H 1.26, N 4.39; found: C 15.23, H 1.40, N 4.36.

N-Hydroxysuccinimide Fatty Acid Ester Derivatives

To a stirred suspension of N-hydroxysuccinimide thallium(I) salt (10 mmol) in chloroform, acid chloride (10 mmol) in the same solvent was slowly added at room temperature. After stirring for 1h, the suspension of thallium chloride was filtered off, resuspended in chloroform, filtered, and thoroughly washed with the same solvent. The combined filtrate was washed with a small amount of water, dried over sodium sulfate, and evaporated under reduced pressure giving essentially quantitative yields of the products. Also, the thallium salt is reacted with commercially available alkyl or aralkyl chlorocarbonates, or with t-butyl chlorocarbonate as prepared according to the procedure of Woodward et al., Jour. Amer. Chem. Soc., 88, p. 852 (1966). Results are shown in Table 1 for typical derivatives.

Acylamino Acid Esters

The acylamino acid ethyl or methyl esters were prepared under the following conditions. To a solution of 5 mmol of amino acid ester hydrochloride (a suspension in the case of lysine esters) in chloroform, equivalent amounts of active succinimidyl fatty acid ester and triethylamine were added with stirring at room temperature. Stirring was continued for at least 2h, and in some cases overnight.

Free Acylamino Acids

These were prepared under the following general conditions. To an aqueous solution of amino acid equivalent amounts of active succinimidyl ester of fatty acid in acetone or ethanol suspension and 2 equivalents of triethylamine were added. The reaction mixture was stirred at room temperature for at least 2h and in some cases overnight. The products were isolated as described for each separate acylamino acid. Analytical samples were recrystallized from glacial acetic acid and fully characterized as shown in Table 2.

$N^6$-Palmitoyl-L-lysine

To the solution of L-lysine (1 mmol) in water (2 ml) and triethylamine (0.27 ml, 2 mmol) 1 mmol of succinimidyl palmitate (suspended in 2 ml of acetone) was added at room temperature under stirring. Stirring of the reaction mixture was continued for 4h. Triethylamine was removed under reduced pressure, the precipitate was collected by filtration, washed with water and ethanol, crystallized from glacial acetic acid giving an 86% yield of the title compound. Analysis data are given in Table 2.

TABLE 1

Physicochemical constants of succinimidyl esters

| | | | Analysis | | | | | |
|---|---|---|---|---|---|---|---|---|
| | | | Calculated | | | Found | | |
| Ester Group | Composition | Melt Point °C | C | H | N | C | H | N |
| Hexanoate | $C_{10}H_{15}NO_4$ | 55–57 | | | | | | |
| Caprate | $C_{14}H_{23}NO_4$ | 69–70 | 62.43 | 8.61 | 5.20 | 62.52 | 8.52 | 5.05 |
| Myristate | $C_{18}H_{31}NO_4$ | 85–86 | 66.43 | 9.60 | 4.30 | 66.29 | 9.76 | 4.43 |
| Arachidate | $C_{24}H_{43}NO_4$ | 98 | 70.37 | 10.55 | 3.41 | 70.21 | 10.40 | 3.59 |
| Behenate | $C_{26}H_{47}NO_4$ | 88–90 | 71.34 | 10.83 | 3.20 | 71.50 | 10.71 | 3.32 |
| Linoleate | $C_{22}H_{35}NO_4$ | Oily | | | | | | |
| Chloroacetate | $C_6H_6NO_4Cl$ | | 37.62 | 3.16 | 7.31 | 37.63 | 3.10 | 7.37 |
| t-butylcarbonate | — | 98–100* | | | | | | |
| ethyl carbonate | — | 50–51** | | | | | | |
| p-nitrobenzyl carbonate | $C_{12}H_{10}N_2O_7$ | 127 | | 9.27 | | | 9.27 | |

*lit: (Frankel et al, Tetrahedron Letters 39, 4765 (1966). m.p. 98–100°). Infrared spectrum is in accordance with the structure.
**lit: (Gross and Bilk, Ann. 725, 212 (1969). m.p. 50–52°). Infrared spectrum is in accordance with the structure.

TABLE 2

Physicochemical data of $N^6$-acyllysine derivatives

| | | | | | Analysis | | | | | |
|---|---|---|---|---|---|---|---|---|---|---|
| | | | m.p. | $(\alpha)_D^{20}$ | Calculated | | | Found | | |
| Acyl Group | Composition | Yield (%) | in °C | 0.5N KOH-CH$_3$OH | C | H | N | C | H | N |
| Capryloyl | $C_{14}H_{28}N_2O_3 \cdot H_2O$ | 84 | 248 | +4° | 57.91 | 10.41 | 9.64 | 57.80 | 10.36 | 9.18 |
| Caproyl | $C_{16}H_{32}N_2O_3$ | 78 | 234 | +3.8° | 63.96 | 10.73 | 9.32 | 63.56 | 11.14 | 9.77 |
| Lauroyl | $C_{18}H_{36}N_2O_3$ | 80 | 230 | +3.2° | 65.81 | 11.05 | 8.52 | | 11.09 | 8.32 |
| Myristoyl | $C_{20}H_{40}N_2O_3$ | 89 | 221–223 | +3.2° | 67.22 | 11.31 | 7.85 | 67.37 | 11.60 | 7.98 |
| Palmitoyl | $C_{22}H_{44}N_2O_3$ | 85 | 230–234 | +3.3° | 68.70 | 11.53 | 7.28 | 68.42 | 11.22 | 7.05 |
| Stearoyl | $C_{24}H_{48}N_2O_3$ | 93 | 238 | +1.5° | 69.85 | 11.72 | 6.79 | 70.14 | 11.79 | 6.48 |
| t-butyloxycarbonyl | — | 68 | | * | | | | | | |

*Infrared spectrum and melting point was found to be identical to the authentic sample.

From the experiment carried out with 2 mmol of succinimidyl palmitate under the same conditions the title compound was isolated in essentially the same yield. Infrared spectra of both compounds were identical: 1580–1590 cm$^{-1}$ (ionized carboxyl group), 1635 and 1520–1535 (amide bands).

Similarly, the $N^6$-acyllysine derivatives of the other fatty acid groups in Table 1 and of other acid groups have been prepared. Analysis results are summarized in Table 2 for typical compounds.

EXAMPLE 2

$N^6$-Capryloyl-L-lysine ($\epsilon$-N-octanoyl-L-lysine)

To a solution of L-lysine monohydrochloride (1.66 g, 9.1 mmol) in 16 of water, 16 ml of acetone and 3.83 ml (27.3 mmol) of triethylamine, succinimidyl caprylate (2.21 g, 9.1 mmol) was added portion-wise under stirring at room temperature within the period of 1h. Stirring was continued for 3h. The organic solvent was removed in vacuo and the reaction mixture was neutralized using diluted hydrochloric acid and allowed to stand at 0° overnight. The white precipitate was collected by filtration, washed with cold water, dried yielding 2.41 g (97%) of the crude product. Infrared spectrum exhibited typical pattern of ε-N-mono-substituted lysine derivative: 1580–1590 cm$^{-1}$ (ionized carboxyl group), 1635 and 1520–1535 (amide bands). The compound was further purified by washing with ethanol and crystallizing from glacial acetic acid giving 2.08 g (84%) of the pure title compound.

EXAMPLE 3

N$^6$-Caproyl-L-lysine (ε-N-Decanoyl-L-lysine)

Similarly, as in example 2, the title compound was prepared using L-lysine monohydrochloride (7.30 g, 40 mmol) and succinimidyl caprate (10.7 g, 40 mmol) in the presence of triethylamine (16.8 ml, 120 mmol) in 35 ml of water and 36 ml of acetone. The product was washed with cold water and with cold ethanol then dried giving 9.04 g (78%) of the desired compound. Infrared: 1580–1590 cm$^{-1}$ (ionized carboxyl), 1520–1540 and 1640 cm$^{-1}$ (amide bands).

EXAMPLE 4

N$^6$-Stearoyl-L-lysine (ε-N-Octadecanoyl-L-lysine)

The title compound was prepared similarly as shown in example 3 from L-lysine monohydrochloride (0.94 g, 5.1 mmol) and succinimidyl stearate (1.94 g, 5.1 mmol) in the presence of triethylamine (2.15 ml, 15.3 mmol) in 9.4 ml of water and 9.4 ml of acetone. The product was washed with cold water and ethanol and then dried yielding 1.98 g (92.7%) of the title compound. Infrared: 1580–1590 cm$^{-1}$ (ionized carboxyl group), 1635 and 1520–1535 cm$^{-1}$ (amide bands).

EXAMPLE 5

N$^6$-t-butyloxycarbonyllysine

To the solution of 575 mg of lysine monohydrochloride in 2 ml of water, 6.2 ml of 1N methanolic potassium hydroxide was added and then 645 mg of t-butyl succinimidyl carbonate in 3 portions was mixed in over 20 minutes while stirring at room temperature. Stirring was continued for another 2 hours, then the reaction mixture was acidified to pH 5, methanol evaporated and the white precipitate collected by filtration giving 779 mg (quantitative yield) of the crude title compound. This was twice recrystallized from warm water to give 529.7 mg (68%) of pure compound.

Its infrared spectrum in Nujol was identical to that of the authentic sample of N$^6$-t-butyloxycarbonyllysine.

Other similar compounds were prepared according to the method of the invention.

I claim:

1. A method for monoacylation of diamino acids, the acyl group being selected from carboxylic acid and substituted carbonic acid moieties, the acylation occurring preferentially at the terminal amino group remote from the carboxyl group of the amino acid, comprising
   (a) preparing the succinimidyl ester of the selected carboxylic or alkyl or aralkyl carbonic acid;
   (b) reacting, in the presence of a basic catalyst to give a pH of at least about 10 or equivalent high basicity, said succinimidyl ester with the diamino acid, its ester or oligopeptide thereof the amount of basic catalyst or pH being high enough to form the amide linkage between the terminal amino group and the acid without significant acylation of the other unprotected amino group, in an inert liquid medium; and
   (c) recovering the N-acyldiamino acid, ester or oligopeptide thereof as product.

2. The method of claim 1 wherein the diamino acid is selected from the group consisting of lysine, ornithine and α,γ-diaminobutyric acid.

3. The method of claim 1 wherein the acylating ester comprises fatty acyl groups having at least about 6 carbon atoms.

4. The method of claim 1 wherein the acylating ester comprises alkyl oxycarbonyl group suitable as a protecting group for the terminal amino group.

5. The method of claim 1 wherein the pH in step (b) is from about 10 to 12.5.

6. The method of claim 1 wherein in step (a) thereof, N-hydroxysuccinimide in the form of its thallium salt is reacted with selected acyl halide, the thallium halide precipitate separated, and the N-succinimidyl acid ester recovered.

7. The method of claim 1 wherein in step (b) thereof, said reaction takes place at about room temperature in the presence of trialkylamine as catalyst in amounts of at least about 2 equivalents based on the diamino acid.

8. The method of claim 1 wherein in step (c) thereof, the acylated amino acid is recovered by precipitation, filtration or centrifugation, washing and drying thereof.

9. The method of claim 1 wherein after step (b) thereof, N-hydroxysuccinimide remains in the reaction medium and is recycled to step (a).

10. The method of claim 1 wherein the amino acid is lysine and the acyl group is derived from fatty acids having from 8 to 18 carbon atoms.

11. The method of claim 1 wherein
    (a) the thallium salt of N-hydroxysuccinimide in an inert solvent medium is reacted with acylchloride in approximately equimolar amounts, the acyl chloride being selected from fatty acid chlorides and alkylcarbonic acid chlorides, to give the succinimidyl ester, and the thallium chloride precipitate separated;
    (b) said succinimidyl ester is then reacted in an inert solvent medium with lysine, lysine hydrochloride, or lysine ester, in the presence of basic catalyst or alkaline catalyst to give a pH of about 10–12 or equivalent high basicity, the pH subsequently reduced or basic catalyst removed to precipitate reaction product; and
    (c) N-acyllysine or -lysine ester precipitate recovered, the acylation preferentially occurring on the terminal amino group of lysine.

12. The method of claim 11 wherein the basic or alkaline catalyst is triethylamine, which is subsequently removed, after the reaction in step (b), by evaporation under reduced pressure or is neutralized by mineral acid.

* * * * *